US006471953B1

(12) United States Patent
N'Guyen et al.

(10) Patent No.: US 6,471,953 B1
(45) Date of Patent: Oct. 29, 2002

(54) PERMANENT-WAVING PROCESS COMPRISING THE PRELIMINARY APPLICATION OF A COMPOSITION COMPRISING AT LEAST ONE ANIONIC POLYMER

(75) Inventors: Lylan N'Guyen, L'Hay les Roses (FR); Anne Sabbagh, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/604,827

(22) Filed: Jun. 28, 2000

(30) Foreign Application Priority Data

Jun. 28, 1999 (FR) .............................. 99 08245

(51) Int. Cl.⁷ .......................... A61K 7/09; A61K 7/06; A61K 7/00; A45D 7/04
(52) U.S. Cl. .................. 424/70.2; 424/70.1; 424/70.2; 424/70.11; 424/401; 132/204; 132/205
(58) Field of Search ............... 424/401, 70.1, 424/70.2, 70.11; 132/204, 205

(56) References Cited

U.S. PATENT DOCUMENTS

| 2,047,398 A | 7/1936 | Voss et al. |
|---|---|---|
| 2,261,002 A | 10/1941 | Ritter |
| 2,271,378 A | 1/1942 | Searle |
| 2,375,853 A | 5/1945 | Kirby et al. |
| 2,388,614 A | 11/1945 | Kirby et al. |
| 2,454,547 A | 11/1948 | Bock et al. |
| 2,723,248 A | 11/1955 | Wright |
| 2,961,347 A | 11/1960 | Floyd |
| 3,206,462 A | 9/1965 | McCarty |
| 3,227,615 A | 1/1966 | Korden |
| 3,716,633 A | 2/1973 | Viout et al. |
| 3,874,870 A | 4/1975 | Green et al. |
| 3,912,808 A | 10/1975 | Sokol |
| 3,917,817 A | 11/1975 | Vanlerberghe et al. |
| 3,929,990 A | 12/1975 | Green et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,128,631 A | 12/1978 | Lundmark et al. |
| 4,131,576 A | 12/1978 | Iovine et al. |
| 4,137,208 A | 1/1979 | Elliott |
| 4,165,367 A | 8/1979 | Chakrabarti |
| 4,172,887 A | 10/1979 | Vanlerberghe et al. |
| 4,185,087 A | 1/1980 | Morlino |
| 4,197,865 A | 4/1980 | Jacquet et al. |
| 4,217,914 A | 8/1980 | Jacquet et al. |
| 4,240,450 A | 12/1980 | Grollier et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,366,827 A | 1/1983 | Madrange et al. |
| 4,591,610 A | 5/1986 | Grollier |
| 4,638,822 A | 1/1987 | Grollier et al. |
| 4,660,580 A | * 4/1987 | Hoch et al. |
| 4,693,935 A | 9/1987 | Mazurek |
| 4,728,571 A | 3/1988 | Clemens et al. |
| 4,761,273 A | 8/1988 | Grollier et al. |
| 4,972,037 A | 11/1990 | Garbe et al. |
| 5,009,880 A | 4/1991 | Grollier et al. |
| 5,154,918 A | 10/1992 | Maignan et al. |
| 5,225,191 A | 7/1993 | de Labbey |
| 5,570,708 A | 11/1996 | Samain |
| 5,609,168 A | 3/1997 | Kischka et al. |
| 5,833,966 A | 11/1998 | Samain |
| 5,932,201 A | 8/1999 | de Labbey et al. |

FOREIGN PATENT DOCUMENTS

| DE | 23 30 956 | 1/1974 |
|---|---|---|
| DE | 44 04 493 | 1/1995 |
| DE | 197 50 520 | 5/1999 |
| EP | 0 095 238 | 11/1983 |
| EP | 0 122 324 | 10/1984 |
| EP | 0 412 704 | 2/1991 |
| EP | 0 412 707 | 2/1991 |
| EP | 0 440 547 | 8/1991 |
| EP | 0 465 342 | 1/1992 |
| EP | 0 568 695 | 11/1993 |
| EP | 0 582 152 | 2/1994 |
| EP | 0 636 358 | 2/1995 |
| EP | 0 681 828 | 11/1995 |

(List continued on next page.)

OTHER PUBLICATIONS

English language Derwent Abstract of DE 44 04 493. (1995).
English language Derwent Abstract of DE 197 50 520. (1999).

(List continued on next page.)

*Primary Examiner*—Thurman K. Page
*Assistant Examiner*—S. Tran
(74) *Attorney, Agent, or Firm*—Finnegan, Henderson, Farabow, Garrett & Dunner, LLP

(57) ABSTRACT

A subject-matter of the invention is a process for the permanent deformation of the hair comprising the successive application of a reducing composition and then of a neutralizing composition, at least one of these compositions comprising at least one cationic polymer, in which, before the application of the reducing composition, a third separate composition, which is distinct from the reducing and neutralizing compositions and comprises at least one anionic polymer, is applied to the hair in a preliminary way. The hair is rinsed, preferably only after having applied the (or at least one of the) composition(s) comprising the cationic polymer(s).

34 Claims, No Drawings

FOREIGN PATENT DOCUMENTS

| | | |
|---|---|---|
| EP | 0 685 219 | 12/1995 |
| EP | 0 723 772 | 7/1996 |
| FR | 1 222 944 | 6/1960 |
| FR | 1 492 597 | 8/1967 |
| FR | 1 538 363 | 9/1968 |
| FR | 1 564 110 | 4/1969 |
| FR | 1 580 545 | 9/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 439 798 | 5/1980 |
| FR | 2 495 931 | 6/1982 |
| FR | 2 505 348 | 11/1982 |
| FR | 2 530 465 | 1/1984 |
| FR | 2 542 997 | 9/1984 |
| FR | 2 739 279 | 4/1997 |
| FR | 2 769 499 | 4/1999 |
| FR | 2 773 071 | 7/1999 |
| FR | 2 773 072 | 7/1999 |
| GB | 0 839 805 | 6/1960 |
| JP | 5-178728 | 7/1993 |
| JP | 5-178729 | 7/1993 |
| WO | WO 93/10751 | 6/1993 |
| WO | WO 93/23009 | 11/1993 |
| WO | WO 93/23446 | 11/1993 |
| WO | WO 95/00578 | 1/1995 |

OTHER PUBLICATIONS

English language Derwent Abstract of FR 2 077 143. (1971).
English language Derwent Abstract of FR 2 080 759. (1971).
English language Derwent Abstract of FR 2 320 330. (1977).
English language Derwent Abstract of FR 2 336 434. (1977).
English language Derwent Abstract of FR 2 357 241. (1978).
English language Derwent Abstract of FR 2 739 279. (1997).
English language Derwent Abstract of FR 2 769 499. (1999).
English language Derwent Abstract of FR 2 773 071. (1999).
English language Derwent Abstract of FR 2 773 072. (1999).
English language Derwent Abstract of JP 5–178728. (1993).
English language Derwent Abstract of JP 5–178729. (1993).
English language Derwent Abstract of FR 1 564 110.(1969).

* cited by examiner

PERMANENT-WAVING PROCESS COMPRISING THE PRELIMINARY APPLICATION OF A COMPOSITION COMPRISING AT LEAST ONE ANIONIC POLYMER

A subject of the invention is a process for the permanent deformation of the hair comprising the preliminary application of a composition that comprises at least one anionic polymer. The invention is also targeted at the use of such a composition for the permanent waving of the hair before the application of the reducing composition, as well as at a kit comprising, in addition to a reducing composition and a neutralizing composition, a third separate composition comprising at least one anionic polymer.

It is known to use cationic polymers in reducing or neutralizing compositions for the permanent deformation of the hair. It is generally known that these polymers improve the cosmetic properties of the hair after the treatment. For example, the hair's touch is often softer and its appearance smoother than that of hair treated with formulations not comprising such polymers.

But, cationic polymers generally exhibit the disadvantage of rendering the hair lank; the hair becomes soft and lacks strength. Naturally, this is harmful both to the look of the hairstyle and to its hold over time. This is because, contrary to the wish of the person involved, the curls produced by the permanent wave begin to deform and then quickly disappear. Finally, cationic polymers often render the hair difficult to style.

A need therefore exists to find a process for the permanent deformation of the hair, which does not give rise to the disadvantages expressed hereinabove or at least lessens one or more of these disadvantages and which in particular may provide the hair with good cosmetic properties and may also provide the hair with lasting deformations, curls, or ringlets and in addition can render the hair easy to style.

The Inventors have discovered, surprisingly and unexpectedly, that it is possible to solve or at least lessen these problems by the preliminary application to the hair of a composition, which is separate and distinct from the reducing and neutralizing compositions and comprises at least one anionic polymer, before applying the reducing composition for the permanent wave.

A subject of the invention is a process for the permanent deformation of the hair comprising the successive application to the hair of a reducing composition (a) and then of a neutralizing composition (b), at least one of these compositions (a) or (b) comprising at least one cationic polymer, wherein a third composition (c), which is distinct from compositions (a) and (b) and comprises at least one anionic polymer, is applied to the hair before the application of the reducing composition (a). The hair is rinsed, preferably only after having applied the (or at least one of the) composition(s) comprising the cationic polymer(s). As would be apparent to one of ordinary skill in the art, the reducing composition (a), neutralizing composition (b), and third composition (c) may be applied to the entire length of the hair.

Another subject of the invention relates to the use in permanent waving of a composition (c) comprising at least one anionic polymer before the application of the reducing composition (a).

Another subject of the invention relates to a kit comprising a first separate compartment comprising a reducing composition (a) and second separate compartment comprising a neutralizing composition (b), wherein at least one of the reducing composition (a) and neutralizing composition (b) comprises at least one cationic polymer, and further wherein the kit additionally comprises a third separate compartment comprising a third composition (c) comprising at least one anionic polymer.

According to one of the advantageous embodiments of the process according to the invention, only the reducing composition (a) comprises a cationic polymer and rinsing is optionally carried out between the application of the reducing composition (a) and of the neutralizing composition (b).

According to another one of the advantageous embodiments of the process according to the invention, only the neutralizing composition (b) comprises a cationic polymer. In this case, the hair is preferably not rinsed between the application of the reducing composition (a) and of the neutralizing composition (b).

According to yet another one of the advantageous embodiments of the process according to the invention, the reducing composition (a) and the neutralizing composition (b) both comprise a cationic polymer and rinsing is optionally carried out between the application of the reducing composition (a) and of the neutralizing composition (b). More preferably, rinsing is not carried out between the application of the reducing composition (a) and of the neutralizing composition (b).

More generally still, within the meaning of the present invention, the expression "cationic polymer" denotes any polymer comprising cationic groups or groups that can be ionized to cationic groups.

The preferred cationic polymers are chosen from those that comprise units chosen from primary, secondary, tertiary, and quaternary amine groups. The units can either form part of the main polymer chain and/or be carried by a side substituent directly connected to the latter.

The cationic polymers used generally have a number-average molecular mass ranging from approximately 500 to approximately $5 \times 10^6$ and preferably from approximately $10^3$ to approximately $3 \times 10^6$.

Mention may more particularly be made, among the cationic polymers, of the polymers of the polyamine, polyaminoamide, and poly(quaternary ammonium) type. These are known products.

One family of cationic polymers is that of the silicone cationic polymers. Mention may be made, among these polymers, of:

(A) Silicone polymers corresponding to the following formula (IV):

in which $G^5$, $G^6$, $G^7$, and $G^8$, which are identical or different, are chosen from a hydrogen atom, a phenyl group, an OH group, a $C_1$–$C_{18}$ alkyl group such as methyl, a $C_2$–$C_{18}$ alkenyl group, and a $C_1$–$C_{18}$ alkoxy group; a and a', which are identical or different, denote an integer from 0 to 3, in particular 0; b denotes 0 or 1 and in particular 1; m and n are numbers such that the sum (n+m) varies from 1 to 2000 and especially from 50 to 150; n denotes a number from 0 to 1999 and in particular from 49 to 149; m denotes a number from 1 to 2000 and in particular from 1 to 10; $R^6$, $R^7$, and $R^8$, which are identical or different, are chosen from monovalent groups of the formula:

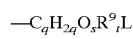

in which q is an integer from 1 to 18; s and t, which are identical or different, are equal to 0 or to 1; each $R^9$ is identical or different and is chosen from optionally hydroxylated alkylene groups; and each L is identical or different and is an optionally quaternized amino group chosen from —NR"—CH$_2$—CH$_2$—N'(R")$_2$, —N(R")$_2$, —N⊕(R")$_3$A$^-$, —N⊕H(R")$_2$A$^-$, —N⊕H$_2$(R")$_2$A$^-$, and —N(R")—CH$_2$—CH$_2$—N⊕R"H$_2$A$^-$ in which each R" is identical or different and is chosen from a hydrogen atom, a phenyl group, a benzyl group, and saturated monovalent hydrocarbonaceous groups for example alkyl groups having from 1 to 20 carbon atoms; and A$^-$ represents a halide ion, such as, for example fluoride, chloride, bromide, or iodide. As used hereinafter, alkylene refers to divalent alkyl groups.

Products corresponding to this definition are, for example, the polysiloxanes named "amodimethicone" in the CTFA dictionary which correspond to the following formula (V):

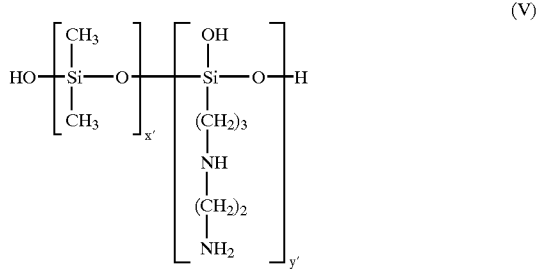

(V)

in which x' and y' are integers depending on the molecular weight, generally such that the said molecular weight ranges from approximately 5000 to approximately 20,000.

A product corresponding to the formula (IV) is the polymer named "trimethylsilylamodimethicone" in the CTFA dictionary, corresponding to the formula:

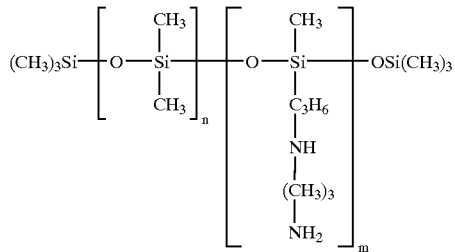

in which n and m have the meanings given above (cf. formula IV).

A commercial product corresponding to this definition is a mixture (90/10 by weight) of a polydimethylsiloxane comprising aminoethylaminoisobutyl groups and of a polydimethylsiloxane sold under the name Q2-8220 by the company Dow Corning.

Such polymers are disclosed, for example, in Patent Application EP-A-95,238, the disclosure of which is incorporated herein by reference.

Other polymers corresponding to the formula (IV) are the silicone polymers corresponding to the following formula (VI):

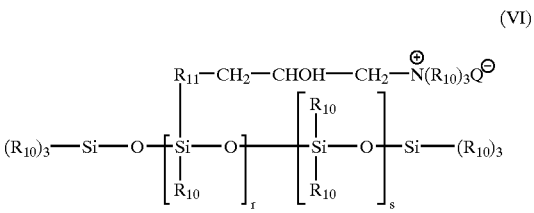

(VI)

in which each R$_{10}$ is identical or different and is chosen from monovalent hydrocarbonaceous groups having from 1 to 18 carbon atoms and in particular C$_1$–C$_{18}$ alkyl and C$_2$–C$_{18}$ alkenyl groups for example a methyl group; each R$_{11}$ is identical or different and is chosen from divalent hydrocarbonaceous groups in particular C$_1$–C$_{18}$ alkylene groups and divalent C$_1$–C$_{18}$ alkyleneoxy groups for example a C$_1$–C$_8$ group; each Q$^-$ is identical or different and is chosen from halide ions in particular chloride ions; r represents a mean statistical value of 2 to 20 and in particular of 2 to 8; s represents a mean statistical value of 20 to 200 and in particular of 20 to 50.

Such polymers are disclosed more particularly in U.S. Pat. No. 4,185,087, the disclosure of which is incorporated herein by reference.

(B) The polymers derived from a compound of the formula: NH—[(CH$_2$)$_3$—Si[OSi(CH$_3$)$_3$]]$_3$ corresponding to the CTFA name "aminobispropyldimethicone".

A polymer coming within this class is the polymer sold by the company Union Carbide under the name "Ucar Silicone ALE 56".

When these silicone polymers are employed, a particularly advantageous embodiment is their joint use with cationic and/or non-ionic surfactants. Use may be made, for example, of the product sold under the name Cationic Emulsion DC 939 by the company Dow Corning, which comprises, in addition to amodimethicone, a cationic surfactant comprising a mixture of products corresponding to the formula (VII):

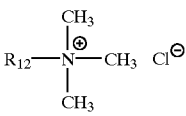

in which R$_{12}$ is chosen from alkenyl and alkyl groups having from 14 to 22 carbon atoms derived from tallow fatty acids, in combination with a non-ionic surfactant of formula:

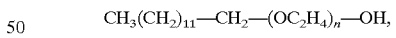

n having a mean value of 20.

Another commercial product which can be used according to the invention is the product sold under the name "Dow Corning Q2 7224" by the company Dow Corning comprising, in combination, the trimethylsilylamodimethicone of formula (IV); a non-ionic surfactant of formula: C$_8$H$_{17}$—C$_6$H$_4$—(OCH$_2$CH$_2$)$_n$—OH, where n=40, also known as octoxynol-40; another non-ionic surfactant of formula: C$_{12}$H$_{25}$—(OCH$_2$—CH$_2$)$_n$—OH, where n=6, also known as isolaureth-6; and glycol.

The polymers of the polyamine, polyaminoamide, or poly(quaternary ammonium) type which can be used in accordance with the present invention which can be mentioned in particular are those disclosed in French Patent Nos. 2,505,348 and 2,542,997, the disclosures of which are incorporated herein by reference. Mention may be made, among these polymers, of:

(1) Optionally quaternized vinylpyrrolidone/dialkylaminoalkyl (meth)acrylate copolymers, such as the products sold under the name "Gafquat®" by the company ISP, such as, for example Gafquat 734, 755, or HS100, or else the product known as "Copolymer 937". These polymers are disclosed in detail in French Patent Nos. 2,077,143 and 2,393,573, the disclosures of which are incorporated herein by reference.

(2) Cellulose ether derivatives comprising quaternary ammonium groups disclosed in French Patent No. 1,492,597, the disclosure of which is incorporated herein by reference, and in particular the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose, which has reacted with an epoxide substituted by a trimethylammonium group.

(3) Cationic cellulose derivatives, such as the copolymers of cellulose or the cellulose derivatives grafted with a water-soluble quaternary ammonium monomer and disclosed in particular in U.S. Pat. No. 4,131,576, the disclosure of which is incorporated herein by reference. Examples include hydroxyalkyl celluloses, for example hydroxymethyl, hydroxyethyl, or hydroxypropyl celluloses grafted in particular with a methacryloylethyltrimethylammonium, methacrylamidopropyltrimethylammonium, or diallyldimethylammonium salt.

The marketed products corresponding to this definition are more particularly the products sold under the name "Celquat L 200" and "Celquat H 100" by the company National Starch.

(4) The cationic polysaccharides disclosed more particularly in U.S. Pat. No. 4,031,307, the disclosure of which is incorporated herein by reference, and more particularly the product sold under the name "Jaguar C. 13 S" by the company Meyhall.

(5) Polymers comprising piperazinyl units and divalent groups chosen from straight-chain and branched-chain, alkylene and hydroxyalkylene groups, optionally interrupted by a spacer group chosen from oxygen, sulphur, nitrogen, aromatic rings, and heterocyclic rings, as well as the oxidation and/or quaternization products of these polymers. Such polymers are disclosed in particular in French Patent Nos. 2,162,025 and 2,280,361, the disclosures of which are incorporated herein by reference.

(6) Water-soluble polyaminoamides prepared in particular by the polycondensation of an acidic compound with a polyamine. These polyaminoamides can be crosslinked by a crosslinking agent chosen from epihalohydrins, diepoxides, dianhydrides, unsaturated dianhydrides, bisunsaturated derivatives, bishalohydrins, bisazetidiniums, bishaloacyidiamines, and alkyl bishalides. Alternatively, these polyaminoamides can be crosslinked by an oligomer resulting from the reaction of a bifunctional compound reactive with respect to a bishalohydrin, a bisazetidinium, a bishaloacyldiamine, an alkyl bishalide, an epihalohydrin, a diepoxide, or a bisunsaturated derivative. The crosslinking agent is used in proportions ranging from 0.025 mol to 0.35 mol per amine group of the polyaminoamide. These polyaminoamides can be alkylated or, if they comprise one or more tertiary amine functional groups, quaternized. Such polymers are disclosed in particular in French Patent Nos. 2,252,840 and 2,368,508, the disclosures of which are incorporated herein by reference.

(7) Polyaminoamide derivatives resulting from the condensation of a polyalkylenepolyamine with a polycarboxylic acid, followed by an alkylation by a bifunctional agent. Mention may be made, for example, of adipic acid/dialkylaminohydroxyalkyl/dialkylenetriamine polymers in which the alkyl group comprises from 1 to 4 carbon atoms and preferably is methyl, ethyl, or propyl. Such polymers are disclosed in particular in French Patent No. 1,583,363, the disclosure of which is incorporated herein by reference.

Mention may more particularly be made, among these derivatives, of the adipic acid/dimethylaminohydroxypropyl/diethylenetriamine polymers sold under the name "Cartaretine F, F4 or F8" by the company Sandoz.

(8) Polymers obtained by reaction of a polyalkylenepolyamine comprising two primary amine groups and at least one secondary amine group with a dicarboxylic acid chosen from diglycolic acid and saturated aliphatic dicarboxylic acids having from 3 to 8 carbon atoms, the molar ratio of polyalkylenepolyamine to dicarboxylic acid is from 0.8:1 to 1.4:1. The polyaminoamide resulting therefrom is reacted with epichlorohydrin in a molar ratio of epichlorohydrin in relation to the secondary amine group of the polyaminoamide of from 0.5:1 to 1.8:1. Such polymers are disclosed in particular in U.S. Pat. Nos. 3,227,615 and 2,961,347, the disclosures of which are incorporated herein by reference.

Polymers of this type are in particular sold under the name "Hercosett 57" by the company Hercules Inc. or else under the name of "PD 170" or "Delsette 101" by the company Hercules in the case of the adipic acid/epoxypropyl/diethylenetriamine copolymer.

(9) Cyclopolymers of methyldiallylamine or of dimethyldiallylammonium, such as the homopolymers or the copolymers comprising, as main constituent of the chain, units corresponding to the formulae (VIII) or (VIII'):

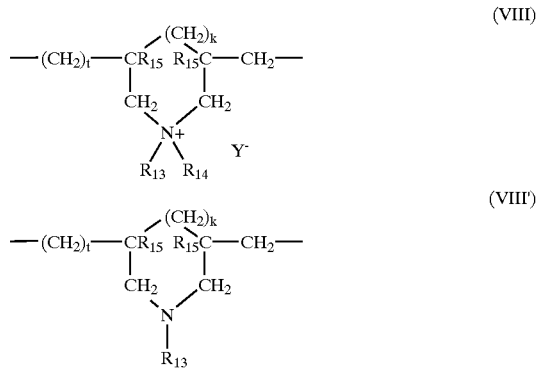

in which k and t are equal to 0 or 1, the sum of k+t being equal to 1; each $R_{15}$ is identical or different and is chosen from a hydrogen atom and a methyl group; $R_{13}$ and $R_{14}$, which are the identical or different, are chosen from an alkyl groups having from 1 to 22 carbon atoms, hydroxyalkyl groups in which the alkyl group preferably has 1 to 5 carbon atoms, and lower amidoalkyl groups or $R_{13}$ and $R_{14}$ can form, jointly with the nitrogen atom to which they are attached, heterocyclic groups such as piperidinyl or morpholinyl; $Y^-$ is an anion, such as bromide, chloride, acetate, borate, citrate, tartrate, bisulphate, bisulphite, sulphate, or phosphate. These polymers are disclosed in particular in French Patent Nos. 2,080,759 and in its Certificate of Addition 2,190,406, the disclosures of which are incorporated herein by reference.

Herein, unless otherwise stated, a lower alkyl group preferably denotes a group having 1 to 8 carbon atoms.

Mention may be made, for example, of the homopolymer of diallyldimethylammonium chloride sold under the name "Merquat 100" by the company Merck and the copolymers of diallyldimethylammonium chloride and of acrylamide sold under the name "Merquat 550".

(10) The di(quaternary ammonium) polymer comprising repeat units corresponding to the formula (IX):

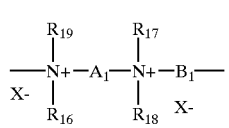

in which $R_{16}$, $R_{17}$, $R_{18}$, and $R_{19}$, which are identical or different, are chosen from aliphatic groups comprising from 1 to 20 carbon atoms, alicyclic groups comprising from 3 to 20 carbon atoms, and arylaliphatic groups comprising from 7 to 20 carbon atoms and lower hydroxyalkyl aliphatic groups or $R_{16}$, $R_{17}$, $R_{18}$, and $R_{19}$, which are identical or different, together or separately, form with the nitrogen atoms to which they are attached, heterocycles optionally comprising a second heteroatom other than nitrogen or else $R_{16}$, $R_{17}$, $R_{18}$, and $R_{19}$, which are identical or different, are chosen from linear and branched $C_1$-$C_6$ alkyl groups substituted by a group chosen from nitrile, ester, acyl, amide, —CO—O—$R_{20}$—D, and —CO—NH—$R_{20}$—D, where $R_{20}$ is an alkylene and D is a quaternary ammonium group; $A_1$ and $B_1$, which are identical or different, are chosen from linear and branched, saturated and unsaturated polymethylene groups comprising from 2 to 20 carbon atoms, which can comprise, bonded to or inserted into the main chain, at least one functional group chosen from aromatic rings, oxygen atoms, sulphur atoms, sulphoxide groups, sulphone groups, disulphide groups, amino groups, alkylamino groups, hydroxyl groups, quaternary ammonium groups, ureido groups, amide groups, and ester groups; and $X^-$ denotes an anion derived from an inorganic or organic acid.

$A_1$, $R_{16}$, and $R_{18}$ can form, with the two nitrogen atoms to which they are attached, a piperazine ring. In addition, if $A_1$ is chosen from linear and branched, saturated and unsaturated, alkylene and hydroxyalkylene groups, $B_1$ can then also be chosen from $(CH_2)_n$—CO—D—OC—$(CH_2)_n$—groups in which D is chosen from:

a) glycol residues of formula: —O—Z—O—, where Z is chosen from linear and branched hydrocarbonaceous groups, or a group corresponding to one of the following formulae:

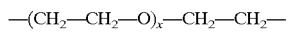

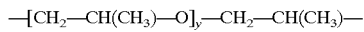

where x and y denote an integer from 1 to 4, representing a defined and unique degree of polymerization, or any number from 1 to 4 representing a mean degree of polymerization;

b) bis-secondary diamine residues such as a piperazine derivative;

c) bis-primary diamine residues of formula: —NH—Y—NH—, where Y is chosen from linear and branched hydrocarbonaceous groups or the divalent group —CH₂—CH₂—S—S—CH₂—CH₂—;

d) ureylene groups of formula: —NH—CO—NH—.

Preferably, $X^-$ is an anion such as chloride or bromide.

These polymers have a number-average molecular weight generally ranging from 1000 to 100,000.

Polymers of this type are disclosed in particular in French Patent Nos. 2,320,330, 2,270,846, 2,316,271, 2,336,434, and 2,413,907 and U.S. Pat. Nos. 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020. The disclosures of these patents are incorporated herein by reference.

(11) Polymers of poly(quaternary ammonium) comprising units of formula (X):

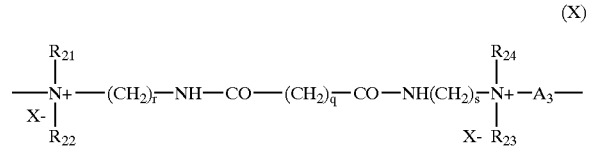

in which $R_{21}$, $R_{22}$, $R_{23}$, and $R_{24}$, which are identical or different, are chosen from a hydrogen atom and methyl, ethyl, propyl, β-hydroxyethyl, β-hydroxypropyl, and —CH₂CH₂(OCH₂CH₂)$_p$OH groups, where p is an integer ranging from 0 to 6, with the proviso that $R_{21}$, $R_{22}$, $R_{23}$, and $R_{24}$ do not simultaneously represent a hydrogen atom; r and s, which are identical or different, are integers ranging from 1 to 6; q is an integer ranging from 0 to 34; X is chosen from halogen atoms; $A_3$ is chosen from groups from a dihalide, preferably —CH₂—CH₂—O—CH₂—CH₂—.

Such compounds are disclosed in particular in Patent Application EP-A-122,324, the disclosure of which is incorporated herein by reference.

Mention may be made among these, for example, of the products "Mirapol® A 15", "Mirapol® AD1", "Mirapol® AZ1", and "Mirapol® 175" sold by the company Miranol.

(12) Homopolymers and copolymers derived from acrylic and methacrylic acids and comprising at least one monomeric unit chosen from:

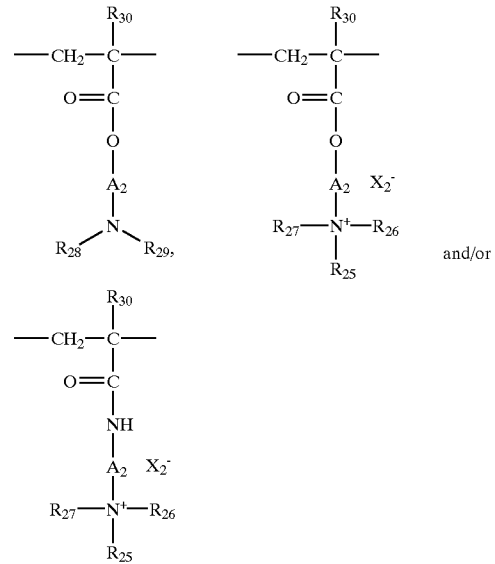

in which each $R_{30}$ group is identical or different and is chosen from H and $CH_3$; each $A_2$ group is identical or different and is chosen from linear and branched alkylene groups of 1 to 6 carbon atoms and hydroxyalkylene groups of 1 to 4 carbon atoms; the $R_{25}$, $R_{26}$, and $R_{27}$ groups, which are identical or different, are chosen from alkyl groups of 1 to 18 carbon atoms and benzyl groups; the $R_{28}$ and $R_{29}$ groups, which are identical or different, are chosen from hydrogen atoms and alkyl groups of 1 to 6 carbon atoms; $X_2^-$ denotes an anion for example methyl sulphate or halide, such as chloride or bromide.

The comonomer or comonomers, which can be used in the preparation of the corresponding copolymers, belong to the family of acrylamides, methacrylamides, diacetone acrylamides, (meth)acrylamides substituted at the nitrogen by lower alkyls, alkyl esters of (meth)acrylic acids, vinylpyrrolidone, or vinyl esters.

(13) Quaternary polymers of vinylpyrrolidone and of vinylimidizole, such as, for example the products sold under the names Luviquat® FC 905, FC 550, and FC 370 by the company BASF.

(14) Polyamines, such as Polyquart H sold by Henkel, referenced under the name "Polyethylene Glycol (15) Tallow Polyamine" in the CTFA dictionary.

(15) Crosslinked polymers of methacryloyloxyethyltrimethylammonium chloride. These include the polymers obtained by homopolymerization of dimethylaminoethyl methacrylate quaternized by methyl chloride or by copolymerization of acrylamide with dimethylaminoethyl methacrylate quaternized by methyl chloride. The homo- or copolymerization is then followed by a crosslinking by a compound possessing olefinic unsaturation, in particular methylenebisacrylamide. Use may more particularly be made of a crosslinked acrylamide/methacryloyloxyethyltrimethylammonium chloride (20/80 by weight) copolymer in the form of a dispersion comprising 50% by weight of the said copolymer in mineral oil. This dispersion is sold under the name of "Salcare SC 92" by the company Allied Colloids. Use may also be made of a crosslinked homopolymer of methacryloyloxyethyltrimethylammonium chloride comprising approximately 50% by weight of the homopolymer in mineral oil. This dispersion is sold under the name of "Salcare® SC 95" by the company Allied Colloids.

Other cationic polymers which can be used in the context of the invention are polyalkyleneimines, in particular polyethyleneimines, polymers comprising vinylpyridine or vinylpyridinium units, condensates of polyamines and of epichlorohydrin, quaternary polyureylenes, and chitin derivatives.

Preference is given, among all the cationic polymers, which can be used in the context of the present invention, to the use of cyclopolymers in particular the dimethyldiallylammonium chloride homopolymers sold under the name "Merquat® 100" by the company Merck or the di(quaternary ammonium) polymers of formula (IX) or of formula (X).

According to the invention, use may also be made of cationic polymers in the latex or pseudolatex form, that is to say in the form of a dispersion of insoluble polymer particles.

According to the invention, at least one cationic polymer can represent from 0.01% to 20% by weight, preferably from 0.1% to 15% by weight and more preferably still from 0.5% to 5% by weight, of the total weight of the final composition.

The anionic polymers generally used are polymers comprising groups derived from carboxylic, sulphonic, or phosphoric acid and have a weight-average molecular weight of ranging from approximately 500 to approximately 5,000,000.

(1) The carboxyl groups are contributed by unsaturated mono- or dicarboxylic acid monomers, such as those corresponding to the formula:

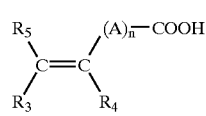

(II)

in which n is an integer from 0 to 10; A denotes a methylene group and when n is greater than 1, at least one A is represented by —LCH$_2$—, where L is a heteroatom such as oxygen or sulphur; R$_5$ is chosen from a hydrogen atom, a phenyl group, and a benzyl group; R$_3$ is chosen from a hydrogen atom, a lower alkyl group, and a carboxyl group; and R$_4$ is chosen from a hydrogen atom, a lower alkyl group, a —CH$_2$—COOH group, a phenyl group, and a benzyl group. In the abovementioned formula, a lower alkyl group preferably denotes a group having 1 to 4 carbon atoms and in particular methyl and ethyl.

The preferred anionic polymers comprising carboxyl groups according to the invention are:

A) homo- or copolymers derived from (meth)acrylic acids and their salts and in particular the products sold under the names Versicol E or K by the company Allied Colloid; Ultrahold by the company BASF; the copolymers derived from acrylic acid and acrylamide sold in the form of their sodium salt under the names Reten 421 423, or 425 by the company Hercules; and the polymers derived from sodium salts of polyhydroxycarboxylic acids.

B) copolymers derived from (meth)acrylic acids and at least one monoethylenic monomer, such as ethylene, styrene, vinyl esters, or esters of (meth)acrylic acid. These copolymers can be grafted onto a polyalkylene glycol, such as polyethylene glycol. Such polymers are disclosed in particular in French Patent No. 1,222,944 and German Application 2,330,956, the disclosures of which are incorporated herein by reference. Mention may in particular be made of the copolymers comprising, in their chain, an optionally N-alkylated and/or N-hydroxyalkylated acrylamide unit, such as disclosed in particular in Luxembourgian Patent Applications 75370 and 75371, the disclosures of which are incorporated herein by reference, or provided under the name Quadramer by the company American Cyanamid. Mention may also be made of copolymers derived from acrylic acid and C$_1$–C$_4$ alkyl methacrylate; terpolymers derived from vinylpyrrolidone, (meth)acrylic acid, and (meth)acrylate of C$_1$–C$_{20}$ alkyl for example of lauryl (such as that sold by the company ISP under the name Acrylidone LM), of tert-butyl (Luviflex VBM 70, sold by BASF), or of methyl (Stepanhold Extra, sold by Stepan); and methacrylic acid/ethyl acrylate/tert-butyl acrylate terpolymers (i.e., terpolymers derived from these named monomers), such as the product sold under the name Luvimer 100 P by the company BASF.

C) copolymers derived from crotonic acid, such as those comprising, in their chain, vinyl acetate or propionate units and optionally other monomers, such as those monomers chosen from allyl and methallyl esters, vinyl ethers, and vinyl esters of linear and branched, saturated carboxylic acids comprising a long hydrocarbonaceous chain, such as those comprising at least 5 carbon atoms. It is optionally possible for these copolymers to be grafted. Additionally, the monomers can be chosen from vinyl, allyl, and methallyl esters of α- and β-cyclic carboxylic acids. Such copolymers are disclosed, inter alia, in French Patent Nos. 1,222,944, 1,580,545, 2,265,782, 2,265,781, 1,564,110, and 2,439,798, the disclosures of which are incorporated herein by reference. Commercial products coming within this class are the Resins 28-29-30, 26-13-14, and 28-13-10 sold by the company National Starch.

D) copolymers derived from $C_4$–$C_8$ monounsaturated carboxylic acids and anhydrides chosen from:

copolymers comprising (i) at least one monomeric unit derived from maleic, fumaric, and itaconic acids and anhydrides and (ii) at least one monomeric unit derived from vinyl esters, vinyl ethers, vinyl halides, phenylvinyl derivatives, acrylic acids, and esters of acrylic acids. The anhydride functional groups of these copolymers optionally are monoesterified or monoamidated. Such polymers are disclosed in particular in U.S. Pat. Nos. 2,047,398, and 2,723,248 and Patent GB 839,805, the disclosures of which are incorporated herein by reference, and in particular those sold under the names Gantrez AN or ES or Avantage CP by the company ISP.

copolymers comprising (i) at least one monomeric unit derived from maleic, citraconic, and itaconic anhydrides and (ii) at least one monomer unit derived from allyl and methallyl esters optionally comprising at least one group chosen from acrylamide, methacrylamide, α-olefin, (meth)acrylic ester, (meth)acrylic acid, and vinylpyrrolidone groups in their chain. The anhydride functional groups of these copolymers optionally are monoesterified or monoamidated. These polymers are, for example, disclosed in French Patent Nos. 2,350,384 and 2,357,241, the disclosures of which are incorporated herein by reference.

E) polyacrylamides comprising carboxylate groups.

(2) The polymers comprising sulpho groups are polymers comprising vinylsulphonic, styrenesulphonic, naphthalenesulphonic, or acrylamidoalkylsulphonic units.

These polymers can in particular be chosen from:

salts of polyvinylsulphonic acid (polymer derived from vinylsulphonic acid) from having a weight-average molecular weight ranging from approximately 1000 to approximately 100,000, as well as copolymers with an unsaturated comonomer, such as (meth)acrylic acids and their esters as well as acrylamide or its derivatives, vinyl ethers, and vinylpyrrolidone.

salts of polystyrenesulphonic acid (polymer derived from styrenesulphonic acid), the sodium salts having a weight-average molecular weight of approximately 500,000 and of approximately 100,000 sold respectively under the names Flexan 500 and Flexan 130 by National Starch. These compounds are disclosed in Patent FR 2,198,719, the disclosure of which is incorporated herein by reference.

salts of polyacrylamidoalkylsulphonic acids (polymer derived from acrylamidosulphonic acid), such as those mentioned in U.S. Pat. No. 4,128,631, the disclosure of which is incorporated herein by reference, and more particularly the polyacrylamidoethylpropanesulphonic acid sold under the name Cosmedia Polymer HSP 1180 by Henkel.

According to the invention, the anionic polymers are preferably chosen from acrylic acid copolymers, such as the acrylic acid/ethyl acrylate/N-tert-butylacrylamide terpolymers sold in particular under the name Ultrahold Strong by the company BASF; copolymers derived from crotonic acid, such as the vinyl acetate/vinyl tert-butylbenzoate/crotonic acid terpolymers and the crotonic acid/vinyl acetate/vinyl neododecanoate terpolymers sold in particular under the name Resin 28-29-30 by the company National Starch; polymers derived from maleic, fumaric, and itaconic acids and anhydrides with vinyl esters, vinyl ethers, vinyl halides, phenylvinyl derivatives, acrylic acids, and esters of acrylic acid, such as the monoesterified methyl vinyl ether/maleic anhydride copolymers sold, for example, under the name Gantrez by the company ISP; the copolymers of methacrylic acid and of methyl methacrylate sold under the name Eudragit L by the company Rohm Pharma; the methacrylic acid/methyl methacrylate/$C_1$–$C_4$ alkyl acrylate/acrylic acid and $C_1$–$C_4$ hydroxyalkyl methacrylate copolymers sold in the form of dispersions under the name Amerhold DR 25 by the company Amerchol or under the name Acudyne 255 by the company Röhm & Haas; the copolymers derived from methacrylic acid and ethyl acrylate sold under the name Luvimer MAEX or MAE by the company BASF; and vinyl acetate/crotonic acid copolymers, the vinyl acetate/crotonic acid copolymers grafted by polyethylene glycol sold under the name Aristoflex A by the company BASF; and (meth)acrylic acid acid homopolymers, sold, for example under the name Versicol E 5.

The most particularly preferred anionic polymers are chosen from the monoesterified methyl vinyl ether/maleic anhydride copolymers sold under the name Gantrez ES 425 by the company ISP; the acrylic acid/ethyl acrylate/N-tert-butylacrylamide terpolymers sold under the name Ultrahold Strong by the company BASF; the copolymers derived from methacrylic acid and methyl methacrylate sold under the name Eudragit L by the company Rohm Pharma; the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; the copolymers derived from methacrylic acid and ethyl acrylate sold under the name Luvimer MAEX or MAE by the company BASF; the vinylpyrrolidone/acrylic acid/lauryl methacrylate terpolymers sold under the name Acrylidone LM by the company ISP; and (meth)acrylic acid homopolymers, sold, for example under the name Versicol E 5.

According to the invention, use may also be made of anionic polymers in the latex or pseudolatex form, that is to say in the form of a dispersion of insoluble polymer particles.

According to the invention, use may also be made of anionic polymers of the grafted silicone type comprising a polysiloxane portion and a non-silicone organic chain portion, one of the two portions constituting the main chain of the polymer and the other being grafted onto said main chain. These polymers are, for example, disclosed in Patent Applications EP-A-0,412,704, EP-A-0,412,707, EP-A-0,640,105, WO 95/00578, EP-A-0,582,152, WO 93/23009 and U.S. Pat. Nos. 4,693,935, 4,728,571, and 4,972,037. The disclosures of these patents and patent applications are incorporated herein by reference.

Such polymers are, for example, the copolymers that can be obtained by radical polymerization of the mixture of monomers composed of:

a) 50% to 90% by weight of tert-butyl acrylate;
b) 1% to 40% by weight of acrylic acid;
c) 5% to 40% by weight of silicone macromer of formula:

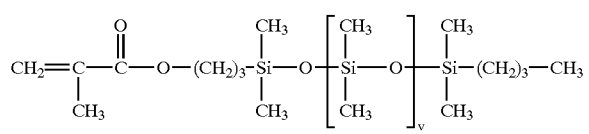

with v being a number ranging from 5 to 700; the percentages by weight being calculated with respect to the total weight of the monomers.

One family of silicone polymers with a polysiloxane skeleton grafted with non-silicone organic monomers, which is suited to the implementation of the present invention, is composed of the silicone polymers comprising, in their structure, the following unit of formula (III):

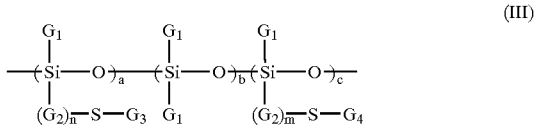

in which the $G_1$ groups, which are identical or different, are chosen from hydrogen atoms, $C_1$–$C_{10}$ alkyl groups, and phenyl groups; the $G_2$ groups, which are identical or different, are chosen from $C_1$–$C_{10}$ alkylene groups; each $G_3$ group is identical or different and is chosen from polymeric residues resulting from the (homo)polymerization of at least one anionic monomer possessing ethylenic unsaturation; each $G_4$ group is identical or different and is chosen from polymeric residues resulting from the (homo)polymerization of at least one hydrophobic monomer possessing ethylenic unsaturation; m and n are equal to 0 or 1; a is an integer ranging from 0 to 50; b is an integer, which can range from 10 to 350; and c is an integer ranging from 0 to 50; with the proviso that at least one of a and c is not 0.

The unit of formula (III) above preferably exhibits at least one, and more preferably still all, of the following characteristics: the $G_1$ groups are chosen from $C_1$–$C_{10}$ alkyl groups preferably the methyl group; n is non-zero; the $G_2$ groups are chosen from divalent $C_1$–$C_3$ groups preferably a propylene group; the $G_3$ group is chosen from polymeric groups resulting from the (homo)polymerization of at least one monomer of a carboxylic acid possessing ethylenic unsaturation type preferably acrylic acid and/or methacrylic acid; the $G_4$ group is chosen from polymeric groups resulting from the (homo)polymerization of at least one monomer of a $C_1$–$C_{10}$ alkyl (meth)acrylate type preferably isobutyl or methyl (meth)acrylate.

The unit of formula (III) above can also preferably exhibit all of the following characteristics: the $G_1$ groups are chosen from $C_1$–$C_{10}$ alkyl groups preferably the methyl group; n is non-zero; the $G_2$ groups are chosen from divalent $C_1$–$C_3$ groups preferably a propylene group; the $G_3$ group is chosen from polymeric groups resulting from the (homo) polymerization of at least one monomer of the carboxylic acid possessing ethylenic unsaturation type preferably acrylic acid and/or methacrylic acid; c is equal to zero.

Examples of grafted silicone polymers include in particular polydimethylsiloxanes (PDMS) on which are grafted, via a connecting link of thiopropylene type, mixed polymer units of the poly((meth)acrylic acid) type and of the poly(alkyl (meth)acrylate) type, such as poly(isobutyl (meth)acrylate). Use is particularly made of the grafted silicone polymers of formula (III) with a polymethyl/methylsiloxane structure comprising poly(methacrylic acid)-3-thiopropyl groups and poly(methyl methacrylate)-3-thiopropyl groups and the grafted silicone polymers of formula (III) with a polymethyl/methylsiloxane structure comprising poly(acrylic acid)-3-thiopropyl groups.

The third composition (c), applied before the reducing composition (a), preferably comprises 0.01% to 20% of anionic polymer, more preferably 0.1% to 10% and more preferably still 0.2% to 5%.

In accordance with the process according to the invention, any kind of reducing composition (a) and neutralizing composition (b) can be used, for example those disclosed in European Patents EP 465,342, EP 440,547, EP 568,695, EP 636,358, EP 681,828, or EP 723,772, or in French Patent Applications published under the numbers FR 2,773,071, FR 2,773,072, and FR 2,769,499. The disclosures of these patent applications are incorporated herein by reference.

Any reducing agent known per se can be used in the composition.

The reducing composition (a) advantageously comprises at least one thiol-comprising reducing agent chosen from thioglycolic acid, thiolactic acid, cysteine, cysteamine, and glyceryl thioglycolate.

Any oxidizing agent known per se can be used in the neutralizing composition (b).

The neutralizing composition (b) advantageously comprises at least one oxidizing agent chosen from hydrogen peroxide, urea hydrogen peroxide, alkali metal bromates, and persalts such as perborates and persulphates.

The reducing composition (a) advantageously comprises, in addition, at least one alkaline agent chosen in particular from aqueous ammonia, monoethanolamine, diethanolamine, triethanolamine, isopropanolamine, 1,3-propanediamine, alkali metal carbonates, alkali metal bicarbonates, ammonium carbonates, ammonium bicarbonates, organic carbonate such as guanidine carbonate, and alkaline hydroxides, which compounds are used alone or as a mixture. The reducing composition (a) can be formulated in one or two parts.

The neutralizing composition (b) and reducing composition (a) preferably comprise, in addition, at least one additive chosen from surfactants, silicones, waxes, thickeners, swelling and penetration agents, fatty alcohols, lanolin derivatives, ceramides, active ingredients, agents for combating hair loss, antidandruff agents, suspending agents, sequestering agents, opacifying agents, colorants, silicone or non-silicone sunscreens, preservatives, and fragrances.

The invention may be better understood with the help of the following non-limiting example which constitutes an advantageous embodiment of the process in accordance with the invention.

The percentages shown in the examples are relative percentages by weight and "A.M." means active material and "OE" means an oxyethylene unit.

EXAMPLE

Example 1

The three compositions described hereinbelow are prepared: a composition comprising an anionic polymer, a reducing composition (a) and a neutralizing composition (b) for a permanent wave.

| Separate composition (c) comprising an anionic polymer: | |
|---|---|
| Methacrylic acid/ethyl acrylate anionic copolymer (50/50) as an aqueous dispersion[1] | 1% AM |
| Monoethanolamine | q.s. pH 7 |
| Demineralized water | q.s. 100 g |
| Reducing composition (a): | |
| The reducer is a two-part reducer. | |
| Part A: powder | |
| Cysteine | 3 g |
| Spruce flour | 5 g |
| Tara flour | 2 g |

-continued

Part B: liquid

| | |
|---|---|
| Monoethanolamine | 2.2 g |
| Fragrance | 0.5 g |
| Oxyethylenated (20 OE) oleyl alcohol[(2)] | 1 g |
| Diethylenetriaminepentaacetic acid, pentasodium salt, as a 40% aqueous solution | 0.4 g |
| Hexadimethrine chloride (Chimex) | 1.2 g A.M. |
| Demineralized water | q.s. 90 g |

Neutralizing composition (b):

| | |
|---|---|
| Aqueous hydrogen peroxide solution | 8% by volume |
| Diallyldimethylammonium chloride homopolymer, as a 40% aqueous solution[(3)] | 1 g A.M. |
| Cocoylamidopropyl dimethyl hydroxypropyl-sulfobetaine, as a 50% aqueous solution[(4)] | 1 g A.M. |
| Citric acid | q.s. pH 3 |
| Demineralized water | q.s. 100 g |

[(1)]Luvimer MAE from BASF
[(2)]Brij 98V from Uniqema
[(3)]Merquat 100 from Calgon
[(4)]Rewoteric Amcas from Witco The separate composition (c), comprising the anionic polymer, is applied to washed and towel-dried hair. The reducing composition (a), after having mixed the parts A and B, is then immediately applied, without rinsing. The hair is shaped with the fingers or using a comb. After a setting time of 15 minutes, still without rinsing the hair, the neutralizing composition (b) is applied. The hair is left to stand for 5 minutes and is then rinsed.

A lasting shaping of the hair is obtained. Its touch is pleasant, cosmetic and full of body. In addition, it is easy to style.

Example 2

The following reducing composition (a) is prepared:

| | |
|---|---|
| Thioglycolic acid | 9 g |
| Diethylenetriaminepentaacetic acid, pentasodium salt, as a 40% aqueous solution | 0.4 g |
| Aqueous ammonia comprising 20% of $NH_3$ | q.s. pH 9 |
| Demineralized water | q.s. for 100 g |

The section composition (c) of Example 1, comprising the anionic polymer, is applied to washed and towel-dried hair. The reducing composition (a) of Example 2 is then immediately applied, without rinsing. After a setting time of 15 minutes, the hair is rinsed and the neutralizing composition (b) of Example 1 is applied. The hair is left to stand for 5 minutes, the curlers are removed and then the hair is rinsed. Lasting and lively curls are obtained. The touch of the hair is pleasant. The hair is easy to style.

What is claimed is:

1. A process for the permanent deformation of the hair comprising applying to the full length of the hair a reducing composition (a) and then applying to the full length of the hair a neutralizing composition (b); wherein at least one of said compositions (a) and (b) comprises at least one cationic polymer; and wherein said process further comprises the application to the full length of the hair of a third composition (c), which is distinct from said compositions (a) and (b) and comprises at least one anionic polymer, before said application of the reducing composition (a) and at least one rinsing of the hair after having applied at least one composition comprising the cationic polymer.

2. The process according to claim 1, wherein only the reducing composition (a) comprises a cationic polymer.

3. The process according to claim 2, wherein the hair is rinsed at least between the application of the reducing composition (a) and of the neutralizing composition (b).

4. The process according to claim 1, wherein only the neutralizing composition (b) comprises a cationic polymer.

5. The process according to claim 1, wherein the reducing composition (a) and the neutralizing composition (b) both comprise a cationic polymer.

6. The process according to claim 5, wherein the hair is rinsed at least between the application of the reducing composition (a) and of the neutralizing composition (b).

7. The process according to claim 1, wherein the at least one anionic polymer of the third composition (c) is chosen from:

(a) polymers comprising carboxyl units derived from unsaturated monocarboxylic or dicarboxylic acid monomers of formula:

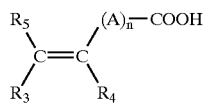

(II)

in which n is an integer from 0 to 10; A denotes a methylene group and when n is greater than 1, at least one A is represented by $-LCH_2-$, where L is a heteroatom; $R_5$ is chosen from a hydrogen atom, a phenyl group, and a benzyl group; $R_3$ is chosen from a hydrogen atom, a lower alkyl group, and a carboxyl group; and $R_4$ is chosen from a hydrogen atom, a lower alkyl group, a $-CH_2-COOH$ group, phenyl group, and benzyl group; and (b) polymers comprising units derived from sulphonic acid.

8. The process according to claim 7, wherein said heteroatom is chosen from oxygen and sulphur atoms.

9. The process according to claim 7, wherein said units derived from sulphonic acid are chosen from vinylsulphonic, styrenesulphonic, and acrylamidoalkylsulphonic units.

10. The process according to claim 1, wherein the at least one anionic polymer of the third composition (c) is chosen from:

A) homo- or copolymers of (meth)acrylic acids and their salts, copolymers derived from acrylic acid and acrylamide and their salts, and polymers derived from sodium salts of polyhydroxycarboxylic acids;

B) copolymers derived from (meth)acrylic acid and at least one monoethylenic monomer optionally grafted onto a polyalkylene glycol, wherein the copolymers of this type comprise in their chain an optionally N-alkylated and/or N-hydroxyalkylated acrylamide unit; copolymers derived from acrylic acid and $C_1-C_4$ alkyl methacrylate; and terpolymers derived from vinylpyrrolidone, acrylic acid, and $C_1-C_{20}$ alkyl methacrylate;

C) copolymers derived from crotonic acid, wherein such copolymers are optionally grafted;

D) copolymers comprising (i) at least one monomeric unit derived from maleic, fumaric, and itaconic acids and anhydrides and (ii) at least one monomeric unit derived from vinyl esters, vinyl ethers, vinyl halides, phenylvinyl derivatives, acrylic acids, and esters of acrylic acids; and copolymers comprising (i) at least one monomeric unit derived form maleic, citraconic, and itaconic anhydrides and (ii) at least one monomeric unit derived from allyl and methallyl esters optionally comprising at least one group chosen from acrylamide, methacrylamide, α-olefin, (meth)acrylic ester, (meth) acrylic acid, and vinylpyrrolidone groups in their chain; wherein the anhydride functional groups of these copolymers are monoesterified or monoamidated;

E) polyacrylamides comprising carboxylate groups.

11. The process according to claim 10, wherein the monoethylenic monomer is chosen from ethylene, styrene, vinyl esters, and esters of (meth)acrylic acid.

12. The process according to claim 10, wherein the polyalkylene glycol is polyethylene glycol.

13. The process according to claim 10, wherein the copolymers of crotonic acid are chosen from those copolymers comprising in their chain units chosen from vinyl acetate or proprionate units and optionally units chosen from allyl esters, methallyl esters, vinyl ether, or vinyl esters of linear and branched saturated carboxylic acids comprising long hydrocarbonaceous chains.

14. The process according to claim 10, wherein the at least one anionic polymer of the third composition (c) is chosen from homopolymers derived from (meth)acrylic acid; copolymers derived from acrylic acid; copolymers derived from crotonic acid; copolymers derived from maleic, fumaric, and itaconic acids and anhydrides and from vinyl esters, vinyl ethers, vinyl halides, phenylvinyl derivatives, acrylic acids, and esters of acrylic acids; copolymers derived from methacrylic acid and methyl methacrylate; copolymers derived from methacrylic acid and ethyl acrylate; vinylpyrrolidone/acrylic acid/lauryl methacrylate terpolymers; vinyl acetate/crotonic acid copolymers; and vinyl acetate/crotonic acid/polyethylene glycol terpolymers.

15. The process according to claim 14, wherein the at least one anionic polymer of the third composition (c) is chosen from acrylic acid/ethyl acrylate/N-tert-butylacrylamide terpolymers, vinyl acetate/vinyl tert-butylbenzoate/crotonic acid terpolymers, crotonic acid/vinyl acetate/vinyl neododecanoate terpolymers, and monoesterified methyl vinyl ether/maleic anhydride copolymers.

16. The process according to claim 1, wherein the at least one anionic polymer of the third composition (c) is chosen from grafted silicone types comprising a polysiloxane portion and a non-silicone organic chain portion, wherein either of the two portions constitutes a main chain of the polymer and the other is grafted onto said main chain.

17. The process according to claim 16, wherein the grafted silicone polymer is chosen from silicone polymers comprising, in their structure, the following unit of formula (III):

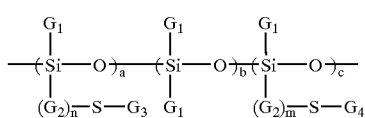

wherein the $G_1$ groups, which are identical or different, are chosen from hydrogen atoms, $C_1$–$C_{10}$ alkyl groups, and phenyl groups; the $G_2$ groups, which are identical or different, are chosen from $C_1$–$C_{10}$ alkylene groups; each $G_3$ group is identical or different and is chosen from polymeric residues resulting from the (homo)polymerization of at least one anionic monomer possessing ethylenic unsaturation; each $G_4$ group is identical or different and is chosen from polymeric residues resulting from the (homo)polymerization of at least one hydrophobic monomer possessing ethylenic unsaturation; m and n are equal to 0 or 1; a is an integer ranging from 0 to 50; b is an integer ranging from 10 to 350; and c is an integer ranging from 0 to 50; with the proviso that at least one of a and c is not 0.

18. The process according to claim 17, wherein said $G_1$ groups are chosen from $C_1$–$C_{10}$ alkyl groups; n is non-zero; said $G_2$ groups are chosen from divalent $C_1$–$C_3$ groups; said $G_3$ group is chosen from polymeric groups resulting from the (homo)polymerization of at least one monomer of a carboxylic acid possessing ethylenic unsaturation type; and said $G_4$ group is chosen from polymeric groups resulting from the (homo)polymerization of at least one monomer of a $C_1$–$C_{10}$ alkyl (meth)acrylate type.

19. The process according to claim 17, wherein said $G_1$ groups are methyl groups; n is non-zero; said $G_2$ groups are propylene groups; said $G_3$ group is chosen from polymeric groups resulting from the (homo)polymerization of at least acrylic acid and/or methacrylic acid; and said $G_4$ group is chosen from polymeric groups resulting from the (homo) polymerization of at least isobutyl (meth)acrylate or methyl (meth)acrylate.

20. The process according to claim 17, wherein said $G_1$ groups are chosen from $C_1$–$C_{10}$ alkyl groups; n is non-zero; said $G_2$ groups are chosen from divalent $C_1$–$C_3$ groups; said $G_3$ group is chosen from polymeric groups resulting from the (homo)polymerization of at least one monomer of a carboxylic acid possessing ethylenic unsaturation type; and c is equal to 0.

21. The process according to claim 1, wherein the at least one anionic polymer of the third composition (c) is chosen from polymers comprising groups derived from carboxylic acid, sulphonic acid, and phosphonic acid.

22. The process according to claim 1, wherein the at least one cationic polymer is chosen from optionally quaternized vinylpyrrolidone/dialkylaminoalkyl (meth)acrylate copolymers, quaternary cellulose ether derivatives, copolymers of cellulose grafted with a water-soluble quaternary ammonium monomer, cationic polysaccharides, polyaminoamides, cyclopolymers, quaternary polymers of vinylpyrrolidone and of vinylimidazole, and silicone cationic polymers.

23. The process according to claim 1, wherein the at least one cationic polymer is chosen from:

(A) silicone polymers corresponding to the following formula (IV):

wherein $G^5$, $G^6$, $G^7$, and $G^8$, which are identical or different, are chosen from a hydrogen atom, a phenyl group, an OH group, a $C_1$–$C_{18}$ alkyl group, a $C_2$–$C_{18}$ alkenyl group, and a $C_1$–$C_{18}$ alkoxy group; a and a', which are identical or different, denote an integer from 0 to 3; b denotes 0 or 1; m and n are numbers such that the sum (n+m) varies from 1 to 2000; n denotes a number from 0 to 1999; m denotes a number from 1 to 2000; $R^6$, $R^7$, and $R^8$, which are identical or different, are chosen from monovalent groups of the formula:

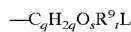

wherein q is an integer from 1 to 18; s and t, which are identical or different, are equal to 0 or to 1; each $R^9$ is identical or different and is chosen from optionally hydroxylated alkylene group; and each L is identical or different and is chosen from optionally quaternized amino groups chosen from —NR"—CH$_2$13 CH$_2$—N'(R")$_2$, —N(R")$_2$, —N$^\oplus$(R")

$_3$A$^-$, —N$^\oplus$H(R")$_2$A$^-$, —N$^\oplus$H$_2$(R")$_2$A$^-$, and —N(R")—CH$_2$—CH$_2$—N$^\oplus$R"H$_2$A$^-$ in which each R" is identical or different and is chosen from a hydrogen atom, a phenyl group, a benzyl group, and a saturated monovalent hydrocarbonaceous group; and A$^-$ represents a halide ion; and (B) polymers derived from a compound of the formula:

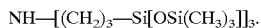

24. The process according to claim 1, wherein the at least one anionic polymer of the third composition (c) is present in an amount ranging from 0.01% to 20% by weight of the third composition (c).

25. The process according to claim 1, wherein the at least one anionic polymer of the third composition (c) is present in an amount ranging from 0.1% to 10% by weight of the third composition (c).

26. The process according to claim 1, wherein the at least one anionic polymer of the third composition (c) is present in an amount ranging from 0.2% to 5% by weight of the third composition (c).

27. The process according to claim 1, wherein the reducing composition (a) further comprises at least one reducing agent chosen from thioglycolic acid, thiolactic acid, cysteine, cysteamine, and glyceryl thioglycolate.

28. The process according to claim 1, wherein the neutralizing composition (b) further comprises at least one oxidizing agent chosen from hydrogen peroxide, urea hydrogen peroxide, alkali metal bromates, and persalts.

29. The process according to claim 28, wherein the persalts are chosen from perborates and persulphates.

30. The process according to claim 1, wherein the reducing composition (a) further comprises at least one alkaline agent chosen from aqueous ammonia, monoethanolamine, diethanolamine, triethanolamine, isopropanolamine, 1,3-propanediamine, alkali metal carbonates, alkali metal bicarbonates, ammonium carbonates, ammonium bicarbonates, organic carbonates, and alkaline hydroxides.

31. The process according to claim 30, wherein the organic carbonate is guanidine carbonate.

32. The process according to claim 1, wherein the reducing composition (a) or the neutralizing composition (b) further comprises at least one additive chosen from surfactants, silicones, waxes, thickeners, swelling and penetration agents, fatty alcohols, lanolin derivatives, ceramides, active ingredients, agents for combating hair loss, antidandruff agents, suspending agents, sequestering agents, opacifying agents, colorants, silicone sunscreens, non-silicone sunscreens, preservatives, and fragrances.

33. A process for the permanent deformation of the hair comprising applying to the full length of the hair a reducing composition (a) and then applying to the full length of the hair a neutralizing composition (b), wherein said process further comprises the application to the full length of the hair of a third composition (c), which is distinct from said compositions (a) and (b) and comprises at least one anionic polymer, before said application of the reducing composition (a).

34. A kit for permanent waving of hair comprising a first separate compartment comprising a reducing composition (a) and a second separate compartment comprising a neutralizing composition (b), wherein at least one of said compositions comprises at least one cationic polymer and wherein said kit further comprises a third separate compartment comprising a third separate composition (c) comprising at least one anionic polymer, wherein said compositions (a), (b), and (c) are separately applied to the full length of said hair.

* * * * *

UNITED STATES PATENT AND TRADEMARK OFFICE
CERTIFICATE OF CORRECTION

PATENT NO.    : 6,471,953 B1
DATED         : October 29, 2002
INVENTOR(S)   : Lylan N'Guyen et al.

It is certified that error appears in the above-identified patent and that said Letters Patent is hereby corrected as shown below:

<u>Title page,</u>
Item [57], ABSTRACT,
Lines 11-12, "polymer (s)" should read -- polymer(s) --;

<u>Column 17,</u>
Line 1, "form" should read -- from --;

<u>Column 18,</u>
Line 67, "-NR-CH$_2$13CH$_2$-N'(R")$_2$," should read -- -NR-CH$_2$-CH$_2$-N'(R")$_2$, --;

<u>Column 18, line 67, to Column 19, line 1,</u>
"–N$^\oplus$(R") $_3$A$^-$," should read -- –N$^\oplus$(R") $_3$A$^-$," --.

Signed and Sealed this

Eighteenth Day of February, 2003

JAMES E. ROGAN
*Director of the United States Patent and Trademark Office*